United States Patent
Kajikawa et al.

(10) Patent No.: US 12,410,109 B2
(45) Date of Patent: Sep. 9, 2025

(54) METHOD FOR PRODUCING OLEFIN AND OLEFINATION REACTION CATALYST

(71) Applicant: DAICEL CORPORATION, Osaka (JP)

(72) Inventors: Yasuteru Kajikawa, Tokyo (JP); Yuuichirou Hirai, Tokyo (JP); Keisuke Ono, Tokyo (JP); Keiichi Tomishige, Sendai (JP); Yoshinao Nakagawa, Sendai (JP)

(73) Assignee: DAICEL CORPORATION, Osaka (JP)

( * ) Notice: Subject to any disclaimer, the term of this patent is extended or adjusted under 35 U.S.C. 154(b) by 95 days.

(21) Appl. No.: 18/028,589

(22) PCT Filed: Sep. 15, 2021

(86) PCT No.: PCT/JP2021/033896
§ 371 (c)(1),
(2) Date: Mar. 27, 2023

(87) PCT Pub. No.: WO2022/065152
PCT Pub. Date: Mar. 31, 2022

(65) Prior Publication Data
US 2023/0339827 A1    Oct. 26, 2023

(30) Foreign Application Priority Data
Sep. 28, 2020    (JP) .................................. 2020-162491

(51) Int. Cl.
*C07C 1/24* (2006.01)
*B01J 23/10* (2006.01)
*B01J 23/68* (2006.01)

(52) U.S. Cl.
CPC ............... *C07C 1/24* (2013.01); *B01J 23/10* (2013.01); *B01J 23/688* (2013.01); *C07C 2523/10* (2013.01); *C07C 2523/68* (2013.01)

(58) Field of Classification Search
CPC ... C07C 1/24; C07C 2523/10; C07C 2523/68; C07C 2523/36; C07C 2523/50;
(Continued)

(56) References Cited

FOREIGN PATENT DOCUMENTS

| JP | 8-59645 A | 3/1996 |
|---|---|---|
| JP | 2000-63302 A | 2/2000 |

(Continued)

OTHER PUBLICATIONS

Daicel Corporation, "The report for a demonstration project on manufacturing C4 chemical products from biomass," [online], Mar. 30, 2020, URL: <https://warp.da.ndl.go.jp/info:ndljp/pid/11518682/www.env.go.jp/recycle/R01_003_Daicel.pdf>, 72 pages total, with an English abstract.

(Continued)

*Primary Examiner* — Prem C Singh
*Assistant Examiner* — Francis C Campanell
(74) *Attorney, Agent, or Firm* — Birch, Stewart, Kolasch & Birch, LLP (57) ABSTRACT

Provided is a method capable of producing an olefin with high selectivity and high yield using a vicinal diol as a raw material. A method for producing an olefin includes a step of reacting a compound including two adjacent carbon atoms each containing a hydroxy group with hydrogen and forming an olefin, and in this step, the reaction of the compound including two adjacent carbon atoms each containing a hydroxy group with the hydrogen proceeds in the presence of a catalyst under a condition substantially free of a solvent. The catalyst includes a carrier, at least one oxide supported on the carrier and selected from the group consisting of (Continued)

oxides of group-6 elements and oxides of group-7 elements, and at least one metal supported on the carrier and selected from the group consisting of silver, iridium, and gold.

15 Claims, 2 Drawing Sheets

(58) Field of Classification Search
CPC ........ C07C 2523/52; C07C 1/20; B01J 23/10; B01J 23/688; C07B 61/00
USPC .................................................. 585/609, 610
See application file for complete search history.

(56) References Cited

FOREIGN PATENT DOCUMENTS

| | | |
|---|---|---|
| JP | 2000-297083 A | 10/2000 |
| JP | 2009-107949 A | 5/2009 |
| JP | 2012-232903 A | 11/2012 |
| JP | 2017-51941 A | 3/2017 |
| JP | 2017051941 A * | 3/2017 |
| WO | WO2011/108509 A1 | 9/2011 |

OTHER PUBLICATIONS

International Preliminary Report on Patentability, dated Mar. 28, 2023, and Written Opinion of the International Searching Authority, dated Nov. 16, 2021 (Forms PCT/IB/373 and PCT/ISA/237) for International Application No. PCT/JP2021/033896, with an English translation.
International Search Report (Form PCT/ISA/210) for International Application No. PCT/JP2021/033896, dated Nov. 16, 2021, with an English translation.
"The report for a demonstration project on manufacturing C4 chemical products from biomass," Daicel Corp., Mar. 30, 2020, p. 157, with English translation.
Taiwanese Office Action and Search Report for counterpart Taiwanese Application No. 110135326, dated Apr. 2, 2025.

* cited by examiner

METHOD FOR PRODUCING OLEFIN AND OLEFINATION REACTION CATALYST

TECHNICAL FIELD

The present disclosure relates to a method for producing an olefin using a vicinal diol as a raw material. The present disclosure also relates to a catalyst for use in the production of an olefin using a vicinal diol as a raw material. The present patent application claims priority from the Japanese patent application No. 2020-162491 filed in Japan on Sep. 28, 2020, the content of which is incorporated herein by reference.

BACKGROUND ART

Unsaturated compounds, including alcohols with carbon-carbon unsaturated bonds in the molecules (unsaturated alcohols) such as allyl alcohol, and ethers with carbon-carbon unsaturated bonds in the molecules (unsaturated ethers) such as dihydrofuran, are important compounds for use in synthetic intermediates, medicaments, agricultural chemicals, fragrances, and the like.

For example, allyl alcohol, one of the unsaturated alcohols, is mainly produced by a production method using an isomer of propylene oxide, or a production method through a reaction of allyl chloride and water (e.g., see Patent Documents 1 and 2). Further, dihydrofuran, one of the unsaturated ethers, is known to be produced by isomerization of epoxy butene (e.g., see Patent Documents 3 to 5).

In the meantime, at present, to produce chemical products, chemical fuel resources, such as mainly petroleum, are consumed in large quantities. That is, in the present society, the current status is that carbon is released unilaterally from the ground to the atmosphere. As a result, issues such as global warming and depletion of fossil fuel resources have arisen, and for such issues, the creation of sustainable society, which uses recycled carbon and circulates carbon with the help of photosynthesis of plants, utilizing biomass (e.g., plant-derived resources, such as cellulose, glucose, and vegetable oils) is being sought in recent years.

For example, known is a method for producing allyl alcohol from glycerin using glycerin as a biomass-derived raw material, and using an iron oxide-based composite oxide catalyst in which an alkali metal is supported on a composite oxide of at least one of zirconia, titania, or alumina and iron oxide (see Patent Document 6).

CITATION LIST

Patent Document

Patent Document 1: JP 2009-107949 A
Patent Document 2: JP 2012-232903 A
Patent Document 3: JP 2000-297083 A
Patent Document 4: JP 2000-63302 A
Patent Document 5: JP H08-59645 A
Patent Document 6: WO 2011/108509 A
Patent Document 7: JP 2017-51941 A

SUMMARY OF INVENTION

Technical Problem

However, the method for producing allyl alcohol described in Patent Document 6 uses the biomass-derived raw material glycerin, in addition to olefins such as allyl alcohol and propylene, other components such as hydroxy acetone, carboxylic acid, and aldehyde are also obtained as products, and the selectivity of allyl alcohol or propylene is low.

Patent Document 7 discloses a catalyst with which an olefin can be obtained with high selectivity by using a raw material vicinal diol that can be used as a biomass-derived raw material. However, a method capable of producing an olefin with even higher selectivity and higher yield is expected.

Therefore, an object of the present disclosure is to provide a method capable of producing an olefin with high selectivity and high yield using a vicinal diol as a raw material.

Solution to Problem

As a result of diligent research to solve the above-described issues, the inventors of the present disclosure have found that, in a reaction of a vicinal diol as a raw material, a specific catalyst is used and the conditions are set to be substantially free of a solvent, and thus an olefin corresponding to the vicinal diol is produced with high selectivity and high yield. The present disclosure relates to inventions completed based on these findings.

The present disclosure provides a method for producing an olefin, the method including an olefinating step of reacting a compound including two adjacent carbon atoms each containing a hydroxy group with hydrogen and forming an olefin, in which in the olefinating step, the reaction of the compound including two adjacent carbon atoms each containing a hydroxy group with the hydrogen proceeds in the presence of a catalyst under a condition substantially free of a solvent, the catalyst including a carrier, at least one oxide supported on the carrier and selected from the group consisting of oxides of group-6 elements and oxides of group-7 elements, and at least one metal supported on the carrier and selected from the group consisting of silver, iridium, and gold.

Preferably, the compound including two adjacent carbon atoms each containing a hydroxy group is a liquid under the condition of the reaction, and the olefin is a gas under the condition of the reaction.

The compound including two adjacent carbon atoms each containing a hydroxy group includes a compound having two or more pairs of structures, each structure having two adjacent carbon atoms each containing a hydroxy group, and the olefin to be produced may include an olefin containing each of all the two or more pairs of the adjacent carbon atoms forming a carbon-carbon double bond.

The compound including two adjacent carbon atoms each containing a hydroxy group includes a compound having two pairs of structures, each structure having two adjacent carbon atoms each containing a hydroxy group, and the olefin to be produced may include a diene.

The compound including two adjacent carbon atoms each containing a hydroxy group may contain erythritol, and the olefin to be produced may include 1,3-butadiene.

Preferably, the olefin is produced with a selectivity of 70% or greater in the olefinating step.

Preferably, the at least one oxide selected from the group consisting of oxides of group-6 elements and oxides of group-7 elements includes rhenium oxide.

Preferably, the carrier includes at least one inorganic oxide selected from the group consisting of cerium oxide, silica, magnesia, zinc oxide, alumina, zirconia, and titania.

Preferably, the catalyst includes the carrier, a film of at least one oxide supported on the carrier and selected from the group consisting of oxides of group-6 elements and oxides of group-7 elements, and a film of at least one metal supported on the carrier and selected from the group consisting of silver, iridium, and gold.

Preferably, a reaction time in the olefinating step is from 10 to 60 hours.

Preferably, a reaction temperature in the olefinating step is from 50 to 250° C.

In addition, the present disclosure provides a catalyst for an olefination reaction, the catalyst, to be used in a reaction of a compound including two adjacent carbon atoms each containing a hydroxy group with hydrogen forming an olefin, including a carrier, a film of at least one oxide supported on the carrier and selected from the group consisting of oxides of group-6 elements and oxides of group-7 elements, and a film of at least one metal supported on the carrier and selected from the group consisting of silver, iridium, and gold.

Advantageous Effects of Invention

According to the method for producing an olefin of the present disclosure, use of a vicinal diol as a raw material enables production of an olefin corresponding to the vicinal diol with high selectivity and high yield. Further, since no solvent is used in the olefination reaction, the cost of recovering the solvent and the cost of supplementing the altered solvent will be unnecessary, thereby simplifying facilities. Furthermore, when a biomass-derived raw material is used, a biomass-derived olefin can be produced with high selectivity by the production method described above. Therefore, in the case where a raw material derived from biomass is used, the load imposed on the environment is small, and such use greatly contributes to the creation of sustainable society.

DESCRIPTION OF EMBODIMENTS

The method for producing an olefin according to embodiments of the present disclosure includes at least a step of reacting a compound including two adjacent carbon atoms each containing a hydroxy group (vicinal diol) with hydrogen in the presence of a specific catalyst under a condition substantially free of a solvent and forming an olefin. In the present specification, "(a step of) reacting a vicinal diol with hydrogen and forming an olefin" may be referred to as an "olefinating (step)". In the olefinating step, an olefin corresponding to the vicinal diol can be produced.

The olefinating step is performed in the presence of a specific catalyst. Thus, an olefin corresponding to the vicinal diol can be produced with high selectivity and high yield in the olefinating step described above.

The olefinating step is performed under conditions substantially free of a solvent. In this case, there is no solvent for dissolving or dispersing a raw material vicinal diol and an olefin product of the olefination reaction. In addition, the produced olefin is poorly soluble or dispersible in the vicinal diol. Accordingly, by performing the olefinating step under conditions substantially free of a solvent, the chance of contact between the olefin and the catalyst is reduced, and further hydrogenation reaction of the formed olefin is suppressed, and thus the olefin can be obtained with high yield and high selectivity. Further, since no solvent is used in the olefination reaction, the cost of recovering the solvent and the cost of supplementing the altered solvent will be unnecessary, thereby simplifying facilities. In the present specification, "solvent" refers to a substance which is a liquid under the reaction conditions, and is a substance other than a raw material vicinal diol and an olefin product.

In the present specification, "substantially free of a solvent" means that a solvent is not actively added to a reaction mixture containing at least a vicinal diol and the catalyst described above. The content ratio of the solvent in the raw material mixture is, for example, 0.1 parts by mass or less, and may be 0.05 parts by mass or less, or 0.01 parts by mass or less, based on the total amount (100 parts by mass) of the vicinal diol.

Examples of the solvent include water and organic solvents. Examples of the organic solvents include alcohols such as methanol, ethanol; isopropanol, n-butanol, and 2-butanol; sulfoxides such as dimethylsulfoxide (DMSO); amides such as dimethylformamide (DMF) and dimethylacetamide (DMAc); ethers such as 1,4-dioxane; esters; ketones; aliphatic hydrocarbons; alicyclic hydrocarbons; aromatic hydrocarbons; and halogenated hydrocarbons.

In the olefinating step, the reaction of vicinal diol and hydrogen may be a reaction of a gas-solid two-phase system that allows gaseous (vaporized) vicinal diol and hydrogen to react in the presence of the catalyst (solid), and may be a reaction of a gas-liquid-solid three-phase system that allows liquid vicinal diol and hydrogen to react in the presence of the catalyst (solid). In particular, the reaction is preferably allowed to proceed in the gas-liquid-solid three-phase system from the viewpoint of further suppressing the compatibility between the vicinal diol and the olefin product, and from the viewpoint of preventing the formation of compounds having a small number of carbons (for example, 3 or less) resulting from a cleavage of a carbon-carbon bond.

More specifically, the reaction of vicinal diol and hydrogen in the olefinating step can be allowed to proceed, for example, by sealing a raw material liquid (not containing a catalyst that is a solid) containing vicinal diol as an essential component in a reactor, and heating in the presence of the catalyst described above. Here, in the olefinating step, one type of the catalyst can be used alone, or two or more types thereof can be used in combination.

The concentration of vicinal diol in the raw material liquid (content ratio of the vicinal diol to 100 mass % of the raw material liquid) is not particularly limited, but is preferably 30 mass % or greater (e.g., from 30 to 100 mass %), more preferably 60 mass % or greater, still more preferably 80 mass % or greater, yet still more preferably 90 mass % or greater, and particularly preferably 99 mass % or greater. When the concentration of vicinal diol is 30 mass % or greater, the reaction rate (conversion) of vicinal diol tends to improve.

Catalyst

The above-mentioned specific catalyst contains a carrier, at least one oxide supported on the carrier and selected from the group consisting of oxides of group-6 elements and oxides of group-7 elements (the oxide may be simply referred to as "oxide"), and at least one metal supported on the carrier and selected from the group consisting of silver, iridium, and gold.

Examples of the group-6 elements include chromium (Cr), molybdenum (Mo), tungsten (W), and praseodymium (Pr). Examples of the group-7 elements include manganese (Mn), technetium (Tc), rhenium (Re), and neodymium (Nd). Among them, the metal constituting the oxide (metal oxide) supported on the carrier in the catalyst described above is preferably group-7 element, and more preferably rhenium. Here, one of the oxide can be used alone, or two or more can be used in combination.

A well-known or commonly used carrier for a catalyst can be used as the carrier for the catalyst and the carrier is not particularly limited. Examples thereof include an inorganic carrier, such as an inorganic oxide or activated carbon; and an organic carrier, such as an ion exchange resin. Among them, an activated carbon and inorganic oxide are preferred from the viewpoint of the reaction activity.

A well-known or commonly used activated carbon can be used as the activated carbon, and the activated carbon is not particularly limited. The activated carbon obtained from any raw material, such as plant-based, mineral-based, and resin-based, can be used. Commercially available products can be also used as the activated carbon, for example, such as those under trade name "Vulcan XC72" (available from CABOT Corporation), trade name "BP2000" (available from CABOT Corporation), trade name "Shirasagi FAC-10" (available from Japan Envirochemicals, Ltd.), trade name "Shirasagi M" (available from Japan Envirochemicals, Ltd.), trade name "Shirasagi C" (available from Japan Envirochemicals, Ltd.), and trade name "Carboraffin" (available from Japan Envirochemicals, Ltd.).

A well-known or commonly used inorganic oxide can be used as the inorganic oxide and the inorganic oxide is not particularly limited. Examples thereof include cerium oxide ($CeO_2$), titania ($TiO_2$), zirconia ($ZrO_2$), magnesia (MgO), zinc oxide (ZnO), silica ($SiO_2$), alumina ($Al_2O_3$), and a complex of two or more types of these inorganic oxides (e.g., such as zeolites). Among them, at least one inorganic oxide (inorganic metal oxide) selected from the group consisting of cerium oxide, silica, magnesia, zinc oxide, alumina, zirconia, and titania is preferred from the viewpoint that the selectivity of an olefin product is more excellent. In particular, cerium oxide, silica, alumina, zirconia, and titania are preferred, and cerium oxide is more preferred from the viewpoint that when the vicinal diol is erythritol, the selectivity of a 1,3-butadiene product is more excellent. Here, one type of the inorganic oxide can be used alone, or two or more types thereof can be used in combination.

Commercially available products can also be used as the inorganic oxide, for example, such as those under trade name "TIO-4" (titania, available from Nippon Aerosil Ltd.), trade name "500 A" (magnesia, available from Ube Industries, Ltd.), trade name "G-6" (silica, available from Fuji Silysia Chemical Ltd.), trade name "KHO-24" (alumina, available from Sumitomo Chemical Co., Ltd.), and trade name "Zirconia" (available from Wako Pure Chemical Industries, Ltd.).

The specific surface area of the carrier is not particularly limited, but is preferably 50 $m^2/g$ or greater (e.g., from 50 to 1500 $m^2/g$, preferably from 100 to 1000 $m^2/g$) in that the above oxide or a particular metal to be described later is well dispersed, aggregation thereof can be prevented, and the catalytic activity per unit mass can be improved. When the specific surface area of the carrier is within the above range, the catalytic activity per unit mass tends to further improve.

The average particle size of the carrier is not particularly limited, but is preferably from 100 to 10000 μm and more preferably from 1000 to 10000 μm from the viewpoint of reactivity; and absence of excess pressure loss in the case of carrying out the reaction in a continuous flow format. In addition, the shape of the carrier may be any of a powder form, a granular form, a molded form (molded body form), or the like, and is not particularly limited.

The amount of the oxide supported on the carrier (the total amount of two or more types of oxides in the case where two or more types of oxides are included) (in terms of a metal atom (group-6 or 7 element) constituting the oxide) is not particularly limited, but is preferably from 0.01 to 50 mass %, more preferably from 0.05 to 30 mass %, still more preferably from 0.1 to 10 mass %, and particularly preferably from 0.15 to 3 mass %, based on the total amount of the oxide, the particular metal, and the carrier (100 mass %). When the oxide is supported in an amount of 0.01 mass % or greater, the selectivity and yield of a particular olefin tend to further improve. In the meantime, when the oxide is supported in an amount of 50 mass % or less, the conversion of vicinal diol tends to improve, and the yield of a particular olefin tends to improve. It is presumed that this is because the smaller the amount of the oxide supported within the above range, the smaller the particle size of the particular metal (to be described later) supported on the carrier tends to be, and this results in relatively increased catalytic activity, catalyst life, and selectivity of the corresponding olefin.

The method for supporting the oxide on the carrier is not particularly limited, and it can be supported on the carrier by a well-known or commonly used method for supporting. Specifically, examples thereof include an impregnation method, a co-precipitation method, and a deposition-precipitation method. Among them, an impregnation method is preferred from the viewpoint of improving the conversion of vicinal diol and improving the yield of a particular olefin.

In the impregnation method, the oxide may be supported on the carrier by impregnating a carrier or a carrier on which the particular metal to be described later is supported with a solution containing group-6 or 7 element constituting the oxide (e.g., an aqueous solution of ammonium perrhenate in the case of rhenium); then subjecting to drying and calcining (preferably calcining in air); and further subjecting to reduction with hydrogen or the like as necessary. Here, in the impregnation method, the amount of the oxide supported can be controlled by adjusting the concentration of the solution containing the group-6 or 7 element described above, impregnation into the carrier, and the number of drying treatment and calcination treatment. In addition, in the impregnation method, the temperature for impregnation of the solution containing the group-6 or 7 element, the temperature for drying the carrier impregnated with the solution, and the temperature for calcining the carrier are not particularly limited. Furthermore, the reduction may be performed also in the co-precipitation method or the deposition-precipitation method from the viewpoint of increasing the initial activity of the reaction and possibility of sufficiently exploiting the catalytic performance.

After supporting the oxide on the carrier, the temperature for calcining the carrier or the temperature for reducing the carrier is not particularly limited, but, for example, it is preferably from 400 to 700° C., and more preferably from 450 to 550° C. in an air atmosphere or a hydrogen atmosphere.

After the reduction treatment, passivation may be performed as necessary. Performing passivation tends to facilitate handling of the catalyst. Here, the passivation can be carried out by a well-known or commonly used method and not particularly limited, but, for example, it can be carried out by exposing the carrier to an oxygen atmosphere at a temperature at or near room temperature.

The catalyst further includes at least one type of metal (it may be referred to as "particular metal") selected from the group consisting of silver (Ag), iridium (Ir), and gold (Au), the metal being supported on the carrier. That is; the catalyst is a catalyst containing a carrier, the oxide supported on the carrier, and at least one selected from the group consisting of silver, iridium, and gold supported on the carrier (therefore, the oxide and the particular metal are supported on the carrier (the same carrier)). Among the particular metals, sifter (Ag) is preferred from the viewpoint of further improving the conversion of vicinal diol and the selectivity and yield of olefin (particularly, the conversion of erythritol, the selectivity and yield of 1,3-butadiene). One type of the particular metal can be used alone, or two or more types thereof can be used in combination.

The aspect of the particular metal contained in the catalyst is not particularly limited, but examples thereof include metals, metal salts, metal oxides, metal hydroxides, or an aspect that the metal is contained as a metal complex in a state of being supported on a carrier.

The method for supporting the particular metal on the carrier is not particularly limited, and a well-known or commonly used method for supporting can be used. Specifically, examples thereof include an impregnation method, a co-precipitation method, and a deposition-precipitation method. Among them, an impregnation method and a deposition-precipitation method are preferred from the viewpoint of improving the conversion of vicinal diol.

In the impregnation method, the oxide may be supported on the carrier in the same manner as in the method for supporting the oxide described above. The method includes impregnating a carrier or a carrier on which the oxide is supported with a solution containing the particular metal (e.g., an aqueous solution of chloroauric acid in the case of gold, an aqueous solution of silver(I) nitrate in the case of silver); subjecting to drying and calcining (preferably calcining in air); and further subjecting to reduction with hydrogen or the like as necessary. More specifically, examples thereof include a method of impregnating the carrier on which the oxide is supported with a solution containing the particular metal; subjecting to drying and calcining; and then further subjecting to reduction with hydrogen or the like as necessary. Here, the temperature for impregnation of the solution containing the particular metal, the temperature for drying the carrier impregnated with the solution, the temperature for calcining the carrier, and the temperature for reducing the carrier are not particularly limited. Furthermore, the reduction may be performed also in the co-precipitation method or the deposition-precipitation method from the viewpoint of increasing the initial activity of the reaction and possibility of sufficiently exploiting the catalytic performance.

After supporting the particular metal on the carrier, the temperature for calcining the carrier or the temperature for reducing the carrier is not particularly limited, but, for example, it is preferably from 400 to 700° C. and more preferably from 450 to 550° C. in an air atmosphere or a hydrogen atmosphere.

In addition, the reduction treatment after impregnation of the solution containing the group-6 or 7 element described above and the reduction treatment after impregnation of the solution containing the particular metal can be carried out simultaneously, for example, by heating in a hydrogen atmosphere after impregnating both solutions (e.g., the heating temperature is preferably from 100 to 700° C. and more preferably from 150 to 550° C.).

In the deposition-precipitation method, examples of the method include a method of adjusting the pH of a solution containing the particular metal (e.g., an aqueous solution of chloroauric acid in the case of gold, or an aqueous solution of silver(I) nitrate in the case of silver) with an alkaline aqueous solution as necessary (e.g., adjusting the pH to 6 to 10), adding therein the carrier or a carrier on which the oxide is supported; after a lapse of a predetermined time, washing with water; subjecting to drying and calcining (preferably calcining in air); and then further subjecting to reduction with hydrogen or the like as necessary. Here, the temperature for adjusting the pH with an alkaline aqueous solution, the temperature for drying the carrier, the temperature for calcining the carrier, and the temperature for reducing the carrier are not particularly limited.

Preferred methods for preparing the catalyst include preferably (i) a method of supporting the oxide and the particular metal one after another on a carrier each by the impregnation method; (ii) a method of supporting the particular metal on a carrier by the deposition-precipitation method and then supporting the oxide by the impregnation method; (iii) a method of supporting the oxide on a carrier by the impregnation method and then supporting the particular metal by the deposition-precipitation method; and (iv) a method of preparing a carrier supporting the particular metal by the co-precipitation method, and supporting the oxide thereon by the impregnation method. Here, in the above (i), supporting by the impregnation method may be in the order of supporting the oxide first or supporting the particular metal first. In particular, it is preferable to support the particular metal first. In addition, it is preferable to perform calcination after each of the supporting of the particular metal and supporting of the oxide.

The catalyst preferably includes a carrier, a film of the particular metal supported and formed on the carrier, and a film of the oxide supported and formed on the carrier. The particular metal and the oxide are formed as individual films on the carrier, and thus the selectivity and yield of olefin tend to improve. Such a catalyst can be prepared by performing calcination after supporting the particular metal, and performing calcination after supporting the oxide, in (i) the method of supporting the oxide and the particular metal one after another on a carrier each by the impregnation method. In the meantime, in the case where the particular metal and the oxide are supported one after another without performing calcination, a film in which the particular metal and the oxide are compatible is formed. In particular, the catalyst more preferably includes the film of the particular metal and the film of the oxide film in this order on the carrier. The film of the particular metal is not limited to a film of the particular metal alone, and may be a film of a metal compound such as a film of a metal oxide.

The ratio (molar ratio, in terms of metal) of the elements of groups 6 and 7 constituting the oxide (the total amount of two or more types of elements in the case where two or more types thereof are included) and the particular metal (the total amount of two or more types of particular metals in the case where two or more types thereof are included) [particular metal/elements of groups 6 and 7] is not particularly limited, but is preferably from 0.002 to 50, more preferably from 0.005 to 10, still more preferably from 0.01 to 5, and particularly preferably from 0.01 to 0.7. The amount of the particular metal used can be adjusted appropriately within the above range according to temperature, time, and the like for allowing vicinal diol and hydrogen to react. Here, the ratio of rhenium and silver (molar ratio, in terms of gold) [Au/Re] is particularly preferably within the above range.

The average particle size of the catalyst is not particularly limited, but is preferably from 100 to 10000 µm and more preferably from 1000 to 10000 µm from the viewpoint of reactivity; and absence of excess pressure loss in the case of carrying out the reaction in a continuous flow format. In addition, the shape of the catalyst is not particularly limited, but examples thereof include a powder form, a granular form, and a molded form (molded body form).

Vicinal Diol

The vicinal diol is a compound including at least a structure containing two adjacent carbon atoms each containing a hydroxy group. Furthermore, vicinal diol (unreacted vicinal diol) recovered from a reaction mixture resulting from the olefinating step described later can be reused. The vicinal diol is preferably a liquid under the conditions of the reaction described above.

The vicinal diol preferably has two or more pairs of structures, each structure having two adjacent carbon atoms each containing a hydroxy group, and more preferably has two or more pairs (particularly, two pairs) of structures adjacent to each other, each structure having two adjacent carbon atoms each containing a hydroxy group.

The vicinal diol may be, for example, a vicinal diol produced by chemical synthesis or a vicinal diol obtained using biomass (i.e., vicinal diol derived from biomass). By using a biomass-derived vicinal diol as the vicinal diol, a biomass-derived olefin can be produced.

The vicinal diol is not particularly limited, but is preferably a compound represented by Formula (1) below.

[Chem. 1]

(1)

In Formula (1), $R^1$, $R^2$, $R^3$, and $R^4$ ($R^1$ to $R^4$) may be the same or different and each represent a hydrogen atom, a monovalent organic group, a monovalent oxygen atom-containing group, a monovalent nitrogen atom-containing group, or a monovalent sulfur atom-containing group. Examples of the monovalent organic group include substituted or unsubstituted hydrocarbon groups (monovalent hydrocarbon groups), alkoxy groups, alkenyloxy groups, aryloxy groups, aralkyloxy groups, acyloxy groups, carboxy groups, alkoxycarbonyl groups, aryloxycarbonyl groups, aralkyloxycarbonyl groups, epoxy groups, alkylthio groups, alkenylthio groups, arylthio groups, aralkylthio groups, cyano groups, isocyanato groups, carbamoyl groups, and isothiocyanate groups. At least two groups out of $R^1$ to $R^4$ may be bonded to each other to form a ring.

Examples of the hydrocarbon group include an aliphatic hydrocarbon group, an alicyclic hydrocarbon group; an aromatic hydrocarbon group, and a group in which two or more of those listed above are bonded.

Examples of the aliphatic hydrocarbon group include an alkyl group, an alkenyl group, and an alkynyl group. Examples of the alkyl group include a $C_{1-20}$ alkyl group (preferably a $C_{1-10}$ alkyl group, and more preferably a $C_{1-4}$ alkyl group), such as a methyl group, an ethyl group, a propyl group, an isopropyl group, a butyl group, a hexyl group, an octyl group, an isooctyl group, a decyl group, and a dodecyl group. Examples of the alkenyl group include a $C_{2-20}$ alkenyl group (preferably a $C_{2-10}$ alkenyl group, and more preferably a $C_{2-4}$ alkenyl group), such as a vinyl group, an allyl group, a methallyl group, a 1-propenyl group, an isopropenyl group, a 1-butenyl group, a 2-butenyl group, a 3-butenyl group, a 1-pentenyl group, a 2-pentenyl group, a 3-pentenyl group, a 4-pentenyl group, and a 5-hexenyl group. Examples of the alkynyl group include a $C_{2-20}$ alkynyl group (preferably a $C_{2-10}$ alkynyl group, and more preferably a $C_{2-4}$ alkynyl group), such as an ethynyl group and a propynyl group. Among these, the aliphatic hydrocarbon group is preferably an alkyl group (preferably a $C_{1-20}$ alkyl group, more preferably a $C_{1-10}$ alkyl group, and still more preferably a $C_{1-4}$ alkyl group.

Examples of the alicyclic hydrocarbon group include: a $C_{3-22}$ cycloalkyl group, such as a cyclopropyl group, a cyclobutyl group, a cyclopentyl group, a cyclohexyl group, and a cyclododecyl group; a $C_{3-12}$ cycloalkenyl group, such as a cyclohexenyl group; and a $C_{4-15}$ crosslinked cyclic hydrocarbon group, such as a bicycloheptanyl group and a bicycloheptenyl group.

Examples of the aromatic hydrocarbon group include aryl groups (e.g., a $C_{6-14}$ aryl group, particularly, a $C_{6-10}$ aryl group), such as a phenyl group and a naphthyl group.

Furthermore, examples of the group in which an aliphatic hydrocarbon group and an alicyclic hydrocarbon group are bonded include a cyclohexylmethyl group and a methylcyclohexyl group. Examples of the group in which an aliphatic hydrocarbon group and an aromatic hydrocarbon group are bonded include a $C_{7-8}$ aralkyl group (particularly, a $C_{7-10}$ aralkyl group), such as a benzyl group and a phenethyl group; a $C_{6-10}$ aryl-$C_{2-6}$ alkenyl group, such as a cinnamyl group; a $C_{1-4}$ alkyl-substituted aryl group, such as a tolyl group; and a $C_{2-4}$ alkenyl-substituted aryl group, such as a styryl group.

The hydrocarbon group may be a hydrocarbon group having a substituent (substituted hydrocarbon group). The number of carbons of the substituent in the substituted hydrocarbon group is preferably from 0 to 20, and more preferably from 0 to 10. Examples of the substituent include a halogen atom such as a fluorine atom, a chlorine atom, a bromine atom, and an iodine atom; a hydroxy group; an alkoxy group (preferably a $C_{1-6}$ alkoxy group, and more preferably a $C_{1-4}$ alkoxy group) such as a methoxy group, an ethoxy group, a propoxy group, an isopropyloxy group, a butoxy group, and an isobutyloxy group; an alkenyloxy group (preferably a $C_{2-6}$ alkenyloxy group, and more preferably a alkenyloxy group) such as an allyloxy group; an aryloxy group (preferably a $C_{6-14}$ aryloxy group) that may have a substituent such as a $C_{1-4}$ alkyl group, a $C_{1-4}$ alkenyl group, a halogen atom, a $C_{1-4}$ alkoxy group, or the like on an aromatic ring, such as a phenoxy group, a tolyloxy group, and a naphthyloxy group; an aralkyloxy group (preferably a $C_{7-18}$ aralkyloxy group) such as a benzyloxy group and a phenethyloxy group; an acyloxy group (preferably a $C_{1-12}$ acyloxy group) such as an acetyloxy group, a propionyloxy group, a (meth)acryloyloxy group, and a benzoyloxy group; an alkylthio group (preferably a $C_{1-6}$ alkylthio group, and more preferably a $C_{1-4}$ alkylthio group) such as a mercapto group, a methylthio group and an ethylthio group; an alkenylthio group (preferably a $C_{1-6}$ alkenylthio group, and more preferably a $C_{1-4}$ alkenylthio group) such as an allylthio group; an arylthio group (preferably a $C_{6-14}$ arylthio group) that may have a substituent such as a $C_{1-4}$ alkyl group, a $C_{2-4}$ alkenyl group, a halogen atom, a $C_{1-4}$ alkoxy group, or the like on an aromatic ring, such as a phenylthio group, a tolylthio group, and a naphthylthio group; an aralkylthio group (preferably a $C_{7-18}$ aralkylthio group) such as a benzylthio group, a phenethylthio group; a carboxy group; an alkoxycarbonyl group (preferably a $C_{1-6}$ alkoxycarbonyl group) such as a methoxycarbonyl group, an ethoxycarbonyl group, a propoxycarbonyl group, and a butoxycarbonyl group; an aryloxycarbonyl group (preferably a $C_{6-14}$ aryloxy-carbonyl group) such as a phenoxycarbonyl group, a tolyloxycarbonyl group, and a naphthyloxycarbonyl group; an aralkyloxycarbonyl group (preferably a $C_{7-18}$ aralkyloxy-carbonyl group) such as a benzyloxycarbonyl group; an amino group; a mono- or dialkylamino group (preferably a mono- or di-$C_{1-6}$ alkylamino group) such as a methylamino group, an ethylamino group, a dimethylamino group and a diethylamino group; an acylamino group (preferably a $C_{1-11}$ acylamino group) such as an acetylamino group, a propionylamino group, and a benzoylamino group; an epoxy group-containing group such as a glycidyloxy group; an oxetanyl group-containing group such as an ethyloxetanyloxy group; an acyl group such as an acetyl group, a propionyl group, and a benzoyl group; an oxo group; and a group in which two or more of these are bonded via a $C_{1-6}$ alkylene group as necessary. The number of substituents contained in the substituted hydrocarbon group is not particularly limited.

Examples of the monovalent oxygen atom-containing group include hydroxy groups, alkoxy groups, hydroperoxy groups, alkenyloxy groups, aryloxy groups, aralkyloxy groups, acyloxy groups, isocyanato groups, sulfo groups, carbamoyl groups, and substituted hydrocarbon groups (oxygen atom-containing hydrocarbon groups) in which one or more of these groups are introduced as substituents. Examples of the monovalent nitrogen atom-containing group include amino groups or substituted amino groups (such as mono- or dialkylamino groups and acylamino groups), cyano groups, isocyanato groups, isothiocyanate groups, carbamoyl groups, and substituted hydrocarbon groups (nitrogen atom-containing hydrocarbon groups) in which one or more of these groups are introduced as substituents. Examples of the monovalent sulfur atom-containing group include mercapto groups (thiol groups), sulfo groups, alkylthio groups, alkenylthio groups, arylthio groups, aralkylthio groups, isothiocyanate groups, and substituted hydrocarbon groups (sulfur atom-containing hydrocarbon groups) in which one or more of these groups are introduced as substituents. The above-mentioned monovalent organic groups, monovalent oxygen atom-containing groups, monovalent nitrogen atom-containing groups, and monovalent sulfur atom-containing groups may overlap one another.

Examples of the ring that may be formed by bonding at least two groups among $R^1$ to $R^4$ include an alicyclic hydrocarbon ring, an alicyclic heterocycle, a condensed ring of an alicyclic hydrocarbon ring with an aromatic ring, a condensed ring of an alicyclic heterocycle with an aromatic ring, and two or more condensed rings thereof. Examples of the alicyclic hydrocarbon ring include a $C_{3-10}$ alicyclic hydrocarbon ring (preferably a $C_{4-8}$ alicyclic hydrocarbon ring), such as a cyclopropane ring, a cyclobutane ring, a cyclobutene ring, a cyclopentane ring, a cyclopentane ring, a cyclohexane ring, and a cyclohexene ring. The alicyclic heterocycle is, for example, an alicyclic heterocycle obtained by replacing one or more carbon atoms forming the alicyclic hydrocarbon ring with an oxygen atom, a sulfur atom, a nitrogen atom, or the like. Examples of the alicyclic heterocyclic ring include oxygen atom-containing heterocycles such as an oxirane ring, an oxetane ring, and an oxolane ring. Further, the ring may have a substituent which may be possessed by the substituted hydrocarbon groups described above.

As $R^1$ and $R^2$ in Formula (1) above, particularly, one is a hydrogen atom, and the other is preferably a hydrogen atom, a hydrocarbon group (in particular, an alkyl group), or a monovalent oxygen atom-containing group (in particular, a hydroxy group substituted or an alkoxy group substituted hydrocarbon group). As $R^3$ and $R^4$ in Formula (1) above, particularly, one is a hydrogen atom, and the other is preferably a hydrocarbon group (in particular, an alkyl group) or a monovalent oxygen atom-containing group (in particular, a hydrocarbon group substituted with a hydroxy group or an alkoxy group). Here, $R^1$ or $R^2$ and $R^3$ or $R^4$ may form an alicyclic hydrocarbon ring. When the monovalent oxygen atom-containing group is a hydrocarbon group substituted with an alkoxy group, $R^1$ or $R^2$ and $R^3$ or $R^4$ may form an oxygen atom-containing heterocycle.

The vicinal diol is not particularly limited, but the number of carbons in the vicinal diol is preferably from 2 to 20, more preferably from 3 to 10, and still more preferably from 3 to 8.

As the vicinal diol, 1,4-anhydroerythritol (a compound where in Formula (1), $R^1$ and $R^3$ are each a hydrogen atom, and $R^2$ and $R^4$ form an oxolane ring), glycerin (a compound where in Formula (1), $R^1$ to $R^3$ are each a hydrogen atom, and $R^4$ is a hydroxymethyl group), erythritol (a compound where in Formula (1), $R^1$ to $R^3$ are each a hydrogen atom, and $R^4$ is a 1,2-dihydroxyethyl group), 1,2-octanediol (a compound where in Formula (1), $R^1$ to $R^3$ are each a hydrogen atom, and $R^4$ is a hexyl group), and 1,2-cyclohexanediol (a compound where in Formula (1), $R^1$ and $R^3$ are each a hydrogen atom, and $R^2$ and $R^4$ form a cyclohexane ring) are particularly preferred from the viewpoint that the conversion of the vicinal diol raw material and the selectivity and yield of the olefin product are higher.

1,4-anhydroerythritol (3,4-dihydroxyoxolane) is a compound having a structure formed by dehydration condensation of hydroxyl groups at positions 1 and 4 of erythritol. The above 1,4-anhydroerythritol may be, for example, 1,4-anhydroerythritol produced by chemical synthesis, or may be 1,4-anhydroerythritol derived from saccharides, such as glucose, by fermentation technology, and is not particularly limited. Examples of 1,4-anhydroerythritol derived from the fermentation technology include 1,4-anhydroerythritol produced by intramolecular dehydration reaction of erythritol used as a raw material, the erythritol derived from saccharides, such as glucose, by fermentation technology. The intramolecular dehydration reaction can be carried out by a well-known or commonly used method and is not particularly limited, 1,4-anhydroerythritol (unreacted 1,4-anhydroerythritol) recovered from a reaction mixture resulting from the olefinating step can also be reused.

Glycerin may be, for example, purified glycerin, or may be crude glycerin. In addition, the glycerin may be glycerin chemically synthesized from ethylene, propylene, or the like, or may be glycerin derived from biomass generated by a transesterification reaction of vegetable oil or the like in the production of biodiesel, and is not particularly limited. Here, glycerin (unreacted glycerin) recovered from a reaction mixture resulting from the olefinating step can also be reused.

Olefin

The above-mentioned olefin, that is an olefin produced by reacting the vicinal diol with hydrogen in the presence of the catalyst, is an olefin corresponding to a vicinal diol as a raw material. In the reaction of the olefinating step where the above catalyst is used as a catalyst, an olefin in which adjacent carbon atoms are bonded to the two hydroxy groups in vicinal diol form a carbon-carbon double bond, or an isomer of such an olefin is produced with high efficiency through a reaction (DODH: Deoxy-dehydration) that simultaneously removes two hydroxy groups in vicinal diol. The olefin is preferably a gas under the conditions of the reaction described above.

When the vicinal diol is a compound having two or more pairs of structures, each structure having two adjacent carbon atoms each containing a hydroxy group, the vicinal diol is olefinated to produce an olefin in which at least part of a plurality of adjacent carbon atoms bonded to two hydroxy groups form a carbon-carbon double bond (e.g., an olefin having two or more carbon-carbon double bonds), as well as an isomer of the vicinal diol or the olefin. When the vicinal diol is a compound having two pairs of structures, each structure having two adjacent carbon atoms each containing a hydroxy group, a diene (conjugated diene in the case of vicinal diol having two or more pairs of structures, the two pairs being adjacent to each other), as well as an isomer of the vicinal diol or the diene are produced. The olefin is more likely to react with hydrogen in the reactor. Particularly, in the case of an olefin having two or more carbon-carbon double bonds, a compound in which part of the olefin is hydrogenated is also produced. Further, only part of the two adjacent carbon atoms in the vicinal diol forms a carbon-carbon double bond, and hydroxy groups may remain. However, in the above-described method for producing an olefin that does not substantially use a solvent, the produced olefin (in particular, an olefin in which all the two adjacent carbon atoms of the two or more pairs form a carbon-carbon double bond) is more stably present, and thus the olefin product can be obtained with even higher selectivity (e.g., 70% or greater, particularly 80% or greater) and high yield.

For example, reaction of erythritol and hydrogen can usually produce a variety of compounds, such as butadiene, 1-butene, 2-butene, 2-butene-1,4-diol, 1-butene-3,4-diol, 1,4-butanediol, 1,2-butanediol, and 2,3-butanediol. However, according to a reaction of vicinal diol and hydrogen using the catalyst described above and using no solvent, in the case of using erythritol as the vicinal diol, it is possible to produce, as an olefin product, 1,3-butadiene: an olefin in which adjacent carbon atoms bonded to two hydroxy groups in erythritol form two or more pairs of carbon-carbon double bonds, with high selectivity (e.g., 87% or greater) and high yield.

Under the conditions of the reaction in the olefinating step, the vicinal diol is preferably a liquid, and the olefin is preferably a gas. The solubility of the olefin in the vicinal diol is lower than that in the solvent, and in the absence of the solvent, most of the olefin is present in the gas. Accordingly, after the olefinating step, the chance of contact between the olefin gas and the catalyst is reduced, and further hydrogenation reaction of the formed olefin is suppressed, and thus the olefin can be obtained with high yield and high selectivity.

Hydrogen

The hydrogen (hydrogen gas) can be used in a state of being substantially alone, or can be used in a diluted state with an inert gas, such as nitrogen, argon, or helium. Furthermore, the hydrogen (unreacted hydrogen) recovered from a reaction mixture resulting from the olefinating step described above can be reused.

The amount (content) of the catalyst used is not particularly limited, but is preferably from 0.1 to 300 parts by mass, more preferably from 1 to 200 parts by mass, and still more preferably from 5 to 150 parts by mass, per 100 parts by mass of vicinal diol. When the amount used is 0.1 parts by mass or greater, the effect by using the catalyst tends to be more sufficiently achieved. In the meantime, when the amount used is 300 parts by mass or less, the conversion of vicinal diol tends to increase. It is preferred to include removing the catalyst, such as by filtration, after completion of the reaction.

The reaction of vicinal diol and hydrogen may be allowed to proceed in the coexistence of a solid acid. That is, the raw material liquid may contain a solid acid in addition to vicinal diol and the solvent described above. Here, the solid acid is a solid exhibiting properties of Bronsted acid and/or Lewis acid (either or both of Bronsted acid and Lewis acid) and having Hammett acidity function ($H_0$) of 6.8 or less. A well-known or commonly used solid acid can be used as the solid acid, and the solid acid is not particularly limited. Examples thereof include solids in which inorganic acids or organic acids (e.g., such as organic sulfonic acids) are supported on a carrier (such as silica, alumina, zeolites, and silica-alumina); crystalline metal silicates, such as gallium silicate, aluminosilicate, and borosilicate (e.g., such as a proton type zeolite H-ZSM-5); heteropolyacids or salts thereof; solids in which a heteropoly acid or a salt thereof is supported on a carrier (e.g., such as silica and alumina); acidic metal oxides, such as zirconium oxide ($ZrO_2$) and titanium oxide ($TiO_2$); and polymers having acid groups, such as carboxyl groups and sulfonic acid groups (e.g., such as cation exchange resins). Commercially available products can also be used as the solid acid. The reaction of the vicinal diol and hydrogen described above can be promoted by allowing the reaction to proceed in the coexistence of the solid acid. Here, for the solid acid, one type can be used alone, or two or more types can be used in combination.

In the case where the solid acid is used in the olefinating step, the amount (content) of the solid acid used is not particularly limited, but is preferably from 0.1 to 50 parts by mass and more preferably from 1 to 20 parts by mass, per 100 parts by mass of vicinal diol. In the case of allowing the solid acid to coexist, it is preferred to include removing the solid acid by filtration or the like, after completion of the reaction.

An additional component may be allowed to coexist in the reaction. That is, the raw material liquid may contain an additional component. In addition, the raw material liquid may contain an impurity derived from raw materials of vicinal diol (such as vicinal diol and raw materials thereof). Such an impurity can degrade the catalyst, and thus it may be preferably removed from the raw material liquid by a well-known or commonly used method (e.g., such as distillation, adsorption, ion exchange, crystallization, and extraction).

The raw material liquid is not particularly limited, but is obtained by mixing vicinal diol and, as necessary, a solid acid, and an additional component. A well-known or commonly used stirrer or the like can be used for mixing.

The molar ratio of hydrogen and vicinal diol [hydrogen (mol)/vicinal diol (mol)] subjected to the reaction (the reaction of vicinal diol and hydrogen) is not particularly limited, but is preferably from 1 to 100, more preferably from 1 to 50, and still more preferably from 1 to 30, When the molar ratio is 1 or greater, the reaction rate (conversion) of vicinal diol tends to improve. In the meantime, when the molar ratio is 100 or less, the utility cost for recovering unreacted hydrogen tends to decrease.

The reaction temperature of vicinal diol and hydrogen in the reaction is not particularly limited, but is preferably from 50 to 250° C., more preferably from 60 to 220° C., and still more preferably from 70 to 200° C. When the reaction temperature is 0° C. or higher, the reaction rate (conversion) of vicinal diol tends to improve. In the meantime, when the reaction temperature is 250° C. or lower, vicinal diol is less likely to be decomposed (e.g., cleavage of a carbon-carbon bond), and the yield of the corresponding olefin tends to improve. Here, the reaction temperature may be controlled to be constant (substantially constant) in the reaction or may be controlled to change stepwise or continuously.

The reaction time of vicinal diol and hydrogen in the reaction is not particularly limited, but is preferably from 0.1 to 200 hours, more preferably from 1 to 150 hours, still more preferably from 3 to 100 hours, and particularly preferably from 10 to 60 hours. When the reaction time is 0.1 hours or longer, the reaction rate (conversion) of vicinal diol tends to improve. In the meantime, when the reaction time is 200 hours or shorter, the selectivity of the corresponding olefin tends to improve.

When the vicinal diol is 1,4-anhydroerythritol, the reaction time is not particularly limited, but the reaction time is preferably 30 hours or longer (e.g., longer than 0 minute and equal to or shorter than 30 hours), and more preferably from 1 to 25 hours, from the viewpoint of further improving the selectivity of 2,5-dihydrofuran. In the meantime, from the viewpoint of improving the conversion of 1,4-anhydroerythritol, the reaction time is preferably 6 hours or longer (e.g., from 6 to 200 hours), and more preferably 13 hours or longer (e.g., from 13 to 40 hours).

When the vicinal diol is glycerin, the reaction time is not particularly limited, but the reaction time is preferably 50 hours or shorter (e.g., longer than 0 and equal to or shorter than 50 hours), and more preferably from 1 to 50 hours, from the viewpoint of further improving the selectivity to allyl alcohol. In the meantime, from the viewpoint of improving the conversion of glycerin, the reaction time is preferably 10 hours or longer (e.g., from 10 to 200 hours), and more preferably 20 hours or longer (e.g., from 20 to 50 hours).

The reaction pressure of vicinal diol and hydrogen (hydrogen pressure under the reaction conditions of vicinal diol and hydrogen) in the reaction is not particularly limited, but is preferably from 0.1 to 50 MPa, more preferably from 0.5 to 30 MPa, and still more preferably from 1 to 15 MPa. When the reaction pressure is 0.1 MPa or higher, the reaction rate (conversion) of vicinal diol tends to improve. In the meantime, when the reaction pressure exceeds 50 MPa, the reactor needs to have a high degree of pressure resistance, and thus this tends to increase the production cost.

The reaction can be carried out in any format, such as a batch format, a semi-batch format, and a continuous flow format. In addition, when the amount of an olefin obtained from a predetermined amount of vicinal diol is desired to be increased, a process of separating and recovering unreacted vicinal diol after completion of the reaction for the purpose of recycling may be employed. Employment of this recycling process can increase the amount of an olefin produced when a predetermined amount of vicinal diol is used.

In the olefinating step, a well-known or commonly used reactor can be used as the reactor, and, for example, a batch reactor, a fluidized-bed reactor, and a fixed-bed reactor can be used. As the fixed-bed reactor, for example, a trickle-bed reactor can be used. The trickle-bed reactor is a reactor (fixed-bed continuous reactor) in a configuration having a catalyst-filled layer filled with a solid catalyst in the inside, where a liquid (in the olefinating step, e.g., the raw material liquid) and a gas (in the olefinating step, hydrogen) flow together from above the reactor to the catalyst-filled layer in a downward flow (gas-liquid downward concurrent flow).

Hereinafter, the method for producing an olefin using a trickle-bed reactor is briefly described. First, the raw material liquid and hydrogen are continuously supplied from above the trickle-bed reactor, and then inside the reactor, vicinal diol and hydrogen in the raw material liquid are allowed to react in the presence of the catalyst in the catalyst-filled layer to produce the corresponding olefin (a reaction product). Then, a reaction mixture containing the olefin is continuously taken out from the reaction mixture release line below the trickle-bed reactor, then hydrogen is separated from the reaction mixture with the high-pressure gas-liquid separator as necessary, and then the olefin is purified and isolated in purifying. In addition, hydrogen separated with the high-pressure gas-liquid separator can be supplied through the hydrogen recycle line to the trickle-bed reactor, thereby enabling the reuse thereof in the reaction.

Employment of a trickle-bed reactor as a reactor allows the reaction to proceed in a gas-liquid-solid three-phase system without vaporizing the vicinal diol in the case of the raw material vicinal diol in liquid form, and thus is advantageous from the viewpoint of cost. In addition, the raw material liquid containing vicinal diol flows downward while forming a thin film on the catalyst surface in the trickle-bed reactor, and thus the distance from the interface between the raw material liquid and hydrogen (gas-liquid interface) to the catalyst surface is short. This facilitates the diffusion of hydrogen dissolved in the raw material liquid to the catalyst surface, enabling efficient production of the corresponding olefin. Furthermore, the process of separating the catalyst from the reaction product of vicinal diol and hydrogen is also unnecessary, and a catalyst regeneration procedure is also easy. Thus, the production process is simple and excellent from the viewpoint of cost.

Here, the material, shape, size, and the like (e.g., such as column diameter and column height) of the trickle-bed reactor are not particularly limited, and the trickle-bed reactor can be appropriately selected according to the scale of the reaction and the like from among well-known or commonly used trickle-bed reactors. In addition, the trickle-bed reactor may be a reactor constituted of a single reaction tube, or may be a multi-stage reactor constituted of a plurality of reaction tubes. The number of reaction tubes in the case where the trickle-bed reactor is a multi-stage reactor can be appropriately selected, and is not particularly limited. Moreover, in the case where the trickle-bed reactor is a multi-stage reactor, the reactor may have a plurality of reaction tubes provided in series, or a plurality of reaction tubes arranged in parallel.

Furthermore, the catalyst-filled layer inside the trickle-bed reactor may, as necessary, be divided (separated) and placed in two or more positions, for example, to prevent overheating due to heat of reaction.

The method for producing an olefin may include an additional step as necessary, in addition to the olefinating step. Examples of the additional step include preparing and purifying the raw material liquid before supplying the raw material liquid and hydrogen to the reactor; and separating and purifying a reaction mixture (e.g., a mixture of products, such as vicinal diol, hydrogen, and an olefin) discharged (flown out) from the reactor. Here, these steps may be carried out in a line separate from that for the olefinating step, or may be carried out in a series (in-line) with the olefinating step.

The method for producing an olefin may include, for example, producing vicinal diol, the raw material in the olefinating step, prior to the olefinating step. For example, when 1,4-anhydroerythritol is used as the vicinal diol, the producing vicinal diol includes producing 1,4-anhydroerythritol. The producing 1,4-anhydroerythritol preferably includes producing 1,4-anhydroerythritol particularly by an intramolecular dehydration reaction of erythritol (it may be referred to as the "dehydration reaction").

Dehydration Reaction

The intramolecular dehydration reaction of erythritol in the dehydration reaction can be carried out by a well-known method and is not particularly limited, but the reaction can be allowed to proceed, for example, by heating erythritol in the presence of an acid catalyst. Here, the dehydration reaction may be carried out in a line separate from that for the olefinating step, or may be carried out in a series with the olefinating step.

Erythritol used as a raw material in the dehydration reaction is not particularly limited and may be erythritol produced by chemical synthesis or may be erythritol derived from saccharides, such as glucose, by fermentation technology. Among them, from the viewpoint of reducing the load on the environment, erythritol derived from saccharides, such as glucose, by fermentation technology is preferably used. In addition, erythritol (unreacted erythritol) recovered from a reaction mixture obtained by the dehydration reaction can be reused.

A well-known or commonly used acid can be used as the acid catalyst used in the dehydration reaction, and the acid is not particularly limited. Examples thereof include inorganic acids, such as hydrochloric acid, sulfuric acid, nitric acid, phosphoric acid, polyphosphoric acid, metaphosphoric acid, condensed phosphoric acid, hydrobromic acid, perchloric acid, hypochlorous acid and chlorous acid; organic acids, such as p-toluenesulfonic acid, trichloroacetic acid, trifluoroacetic acid, and trifluoromethanesulfonic acid; and solid acids, such as cation exchange resins, zeolites, silica-alumina, and heteropolyacids (such as phosphomolybdic acid). Among them, solid acids are preferred from the viewpoint of ease of separation from products and the like, and ease of regeneration treatment. Here, commercially available products can be used as the acid catalyst, and, for example, exemplified by commercially available solid acids under trade name "Amberlyst" (available from The Dow Chemical Company) and trade name "Nafion" (available from DuPont de Nemours, Inc.). Here, one type of the acid (acid catalyst) can be used alone, or two or more types thereof can be used in combination.

The reaction (intramolecular dehydration reaction) can be allowed to proceed in the absence of a solvent and can be allowed to proceed in the presence of a solvent. Examples of the solvent include water; alcohols, such as methanol, ethanol; isopropanol, and n-butanol; ethers, such as 1,4-dioxane; and highly polar organic solvents; such as dimethylsulfoxide (DMSO), dimethylforamide (DMF), and dimethylacetamide (DMAc). Among them, from the viewpoint of excellent reactivity; and ease of handling and disposal, at least water is preferably contained as a solvent. Here, one type of the solvent can be used alone, or two or more types thereof can be used in combination. In the case where a solvent is used in the dehydration reaction, the solvent is removed before the subsequent olefinating step.

The reaction temperatures (heating temperatures) of the reaction (intramolecular dehydration reaction) is not particularly limited, but is preferably from 40 to 240° C., more preferably from 80 to 200° C., and still more preferably from 120 to 180° C. Controlling the reaction temperature within the above range can facilitate the intramolecular dehydration reaction of erythritol more efficiently. Here, the reaction temperature may be controlled to be constant (substantially constant) in the reaction or may be controlled to change stepwise or continuously.

The time (reaction time) of the reaction (intramolecular dehydration reaction) is not particularly limited, but is preferably from 1 to 100 hours, more preferably from 2 to 50 hours, and still more preferably from 3 to 30 hours. When the reaction time is less than 1 hour, the reaction rate (conversion) of erythritol may not sufficiently increase. In the meantime, the reaction time exceeding 100 hours may be disadvantageous from the viewpoint of cost.

The reaction (intramolecular dehydration reaction) can be carried out in any atmosphere; such as in an air atmosphere and in an inert gas atmosphere, such as nitrogen or argon. In particular, from the viewpoint of improving the selectivity of 1,4-anhydroerythritol, the reaction is preferably carried out in an inert gas atmosphere. In addition, the reaction (intramolecular dehydration reaction) can be carried out under any of normal pressure, increased pressure, and reduced pressure. In particular, from the viewpoint of improving the conversion of erythritol, the reaction is preferably carried out under increased pressure. For example, in the case where water is used as a solvent, the reaction temperature can be increased to 100° C. or higher by carrying out the reaction under increased pressure, and thus the conversion of erythritol can be efficiently increased.

The reaction (intramolecular dehydration reaction) can be carried in any format, such as a batch format, a semi-batch format, and a continuous flow format.

The dehydration reaction produces 1,4-anhydroerythritol. 1,4-anhydroerythritol thus obtained is then used as a raw material in the olefinating step, but it can be used after being isolated from the reaction mixture obtained by the dehydration reaction by a well-known or commonly used method (e.g., such as distillation, adsorption, ion exchange, crystallization, and extraction), or may be used without being isolated from the reaction mixture (as necessary, after removing the acid catalyst or the like).

Each aspect disclosed in the present specification can be combined with any other feature disclosed herein. Note that each of the configurations, combinations thereof, or the like in each of the embodiments are examples, and additions, omissions, replacements, and other changes to the configurations may be made as appropriate without departing from the spirit of the present disclosure. In addition, each aspect of the invention according to the present disclosure is not limited by the embodiments or the following examples but is limited only by the claims.

EXAMPLES

Hereinafter, embodiments of the present disclosure will be more specifically described with reference to the examples.

Production Example 1

Production of Catalyst ($ReO_x$—$Ag/CeO_2$)

6 mg of silver nitrate (I) ($AgNO_3$, available from FUJI-FILM Wako Pure Chemical Corporation) was diluted with 10 mL of distilled water to prepare a silver(I) nitrate aqueous solution. In addition, 29 mg of ammonium perrhenate ($NH_4ReO_4$, available from Mitsuwa Chemicals Co., Ltd.) was dissolved in 10 mL of distilled water at 20° C. to prepare an ammonium perrhenate aqueous solution. Then, cerium oxide (trade name "HS", available from Daiichi Kigenso Kagaku Kogyo Co., Ltd.) was pre-calcined at 600° C. for 3 hours (heating rate: 10° C./min) in an air atmosphere. Subsequently, to 0.997 g of the calcined cerium oxide heated to 80° C., a total amount of the silver(I) nitrate aqueous solution was added in five portions while preventing liquid pooling, and the mixture was stirred to impregnate. This resulting mixture was dried overnight in a dryer at 110° C. (12 hours or longer), and then calcined in an air atmosphere at 500° C. for 3 hours (heating rate: 10° C./min). To the calcined mixture while being heated to 80° C., a total amount of the ammonium perrhenate aqueous solution was added in live portions while preventing liquid pooling, and the mixture was stirred to impregnate. This resulting mixture was dried overnight in a dryer at 110° C. (12 hours or longer), and then calcined in an air atmosphere at 500° C. for 3 hours (heating rate: 10° C./ruin). In this manner, prepared was a catalyst (ReO$_X$—Ag/CeO$_2$) in which rhenium was supported in an amount of 1 mass % and [Ag/Re]=0.3.

Production Example 2

Production of Catalyst (ReO$_X$/Au/CeO$_2$)

A catalyst (ReO$_X$—Au/CeO$_2$) in which rhenium was supported in an amount of 1 wt. % and [Au/Re]=0.3 was produced in the same manner as in Production Example 1 except that a tetrachloroauric(III) acid aqueous solution prepared by diluting 11 mg of hydrogen tetrachloroaurate (III) tetrahydrate (HAuCl$_4$·4H$_2$O available from FUJIFILM Wako Pure Chemical Corporation) with 10 mL of distilled water was used instead of the silver(1) nitrate aqueous solution and the amount of cerium oxide was 0.975 g.

Example 1

Into a glass autoclave inner cylinder, a stirrer chip, 0.3 g of the weighed catalyst (ReO$_X$—Ag/CeO$_2$) obtained in Production Example 1 and 0.25 g of erythritol were charged. The autoclave inner cylinder was placed in a 190 mL autoclave (high-pressure batch reactor) and the inner lid was closed. The autoclave was covered with the lid with the packing interposed therebetween and tightened using a hexagonal wrench to be sealed. Next, an operation of filling the inside of the autoclave with 1 MPa hydrogen and then evacuating the hydrogen to adjust the pressure to a pressure slightly higher than atmospheric pressure was repeated three times to replace the air in the autoclave with hydrogen. The autoclave was charged with hydrogen to exhibit 5.8 MPa at room temperature, thereby exhibiting 8 MPa at reaction temperature.

Next, the autoclave was set in a heating device with a magnetic stirrer and heated to increase the temperature inside the autoclave to 140° C., and stirred at 250 rpm for a predetermined time while maintaining the reaction temperature at 140° C. The reaction start time was determined at a time when the temperature reached 138° C., i.e., 2° C. lower than the reaction temperature: 140° C. The heating rate was adjusted to allow the heating time to be about 40 minutes.

Thereafter, the reactor was taken out and cooled to about 100° C., in a water bath, and the total amount of the gas in the reactor was recovered. Further, hydrogen was introduced in the same amount as the recovered amount, and then the total amount of the gas in the reactor was recovered again.

After the gas was recovered, the reactor was cooled to room temperature in a water bath, and a recovery solvent (mixed solution of 10 g of 1,4-dioxane and 5 g of water) was added to the autoclave to recover the liquid phase.

Comparative Example 1

An operation was performed in the same manner as in Example 1 except that a stirrer chip, 0.3 g of the weighed catalyst (ReO$_X$—Ag/CeO$_2$) obtained in Production Example 1, 0.25 g of erythritol, and 4 g of 1,4-dioxane were charged into a glass autoclave inner cylinder.

Example 2

An operation was performed in the same manner as in Example 1 except that 0.3 g of the catalyst (ReO$_X$—Au/CeO$_2$) obtained in Production Example 2 was used instead of 0.3 g of the catalyst (ReO$_X$—Ag/CeO$_2$) obtained in Production Example 1.

Comparative Example 2

An operation was performed in the same manner as in Comparative Example 1 except that 0.3 g of the catalyst (ReO$_X$—Au/CeO$_2$) obtained in Production Example 2 was used instead of 0.3 g of the catalyst (ReO$_X$—Ag/CeO$_2$) obtained in Production Example 1.

Analysis (1) Gas Phase Analysis (FID-GC)

0.1 mL of dichloromethane as an internal standard substance was placed in a gas bag filled with the recovered gas, and analyzed by FID and GC-MS analysis using gas chromatography (gas chromatograph: "GC-2025" (available from Shimadzu Corporation), column: Rtx1-PONA, detector: FID). Based on the analysis, the amounts of erythritol and products in the gas phase were calculated. Since 1,3-butadiene and 1-butene could not be separated by FID-GC analysis, separation was performed by the gas phase analysis (GC-MS) below, and the yield and selectivity of these products were calculated. The detailed conditions of the gas chromatography are as follows.

FID-GC Conditions

Column size: 0.25 mm in inside diameter×100 mm in length×0.5 μm in film thickness Column temperature: After maintaining at 40° C. for 25 minutes, the temperature was raised to 240° C. at a heating rate of 100° C./min and held for 12 minutes Vaporizing chamber temperature: 270° C.

Detector temperature: 300° C.

Carrier gas: N$_2$

GC setting parameter

Column inlet pressure: 100.0 kPa

Column flow rate: 0.44 mL/min

Linear velocity: 10.2 cm/sec

Total flow rate: 42.8 mL/min

Split ratio: 90.0

Control mode: pressure (2) Gas Phase Analysis (GC-MS)

The sample subjected to the gas phase analysis (FID-GC) was analyzed by the EI method using gas chromatography (gas chromatograph: "GCMS-QP2010 SE" (available from Shimadzu Corporation), column: Rtx1-PONA). From the analysis result, a ratio of peak areas in MS spectra: 54 MS spectrum for 1,3-butadiene and 56 MS spectrum for 1-butene was calculated, and the amounts of 1,3-butadiene and 1-butene in the gas phase were calculated from the ratio of the peak areas and the total of the areas in the FID-GC. The detailed conditions of the gas chromatography are as follows.

Conditions for GC-MS Analysis
 Column size: 0.25 mm in inside diameter×100 mm in length×0.5 μm in film thickness
 Column temperature: After maintaining at 40° C. for 20 minutes, the temperature was raised to 240° C. at a heating rate of 100° C./min and held for 12 minutes
 Vaporizing chamber temperature: 270° C.
 Detector temperature: 300° C.
 Carrier gas: He
 GC setting parameter
 Column inlet pressure: 900.0 kPa
 Column flow rate: 4.32 mL/min
 Linear velocity: 75.0 cm/sec
 Total flow rate: 396.5 mL/min
 Split ratio: 90.0
 Control mode: pressure (3) Liquid Phase Analysis (FID-GC)

0.1 ml, of dipropylene glycol dimethyl ether as an internal standard substance was added to the recovered liquid phase, and the mixture was filtered through a membrane filter to prepare an analytic sample. This sample was analyzed by FID and GC-MS analysis using gas chromatography (gas chromatograph: "GC-2014" (available from Shimadzu Corporation), column: TC-WAX, detector: FID). Based on the analysis, the amounts of products in the liquid phase were calculated. The detailed conditions of the gas chromatography are as follows.

FID-GC Conditions
 Column size: 0.25 mm in inside diameter×30 mm in length×0.25 μm in film thickness
 Column temperature: After maintaining at 50° C. for 5 minutes, the temperature was raised to 230° C. at a heating rate of 10° C./min and held for 12 minutes
 Vaporizing chamber temperature: 250° C.
 Detector temperature: 240° C.
 Carrier gas: $N_2$
 GC setting parameter
 Column inlet pressure: 75.0 kPa
 Colum flow rate: 0.96 mL/min
 Linear velocity: 25.2 cm/sec
 Total flow rate: 32.7 mL/min
 Split ratio: 30.0
 Control mode: pressure (4) Liquid Phase Analysis (HPLC)

The analytic sample prepared by the liquid phase analysis (FID-GC) was diluted 10-fold with dipropylene glycol dimethyl ether. The resulting sample was analyzed by high performance liquid chromatography ("LC-20A" (available from Shimadzu Corporation), column: Amines HPX-87 H, mobile phase: 0.01 M $H_2SO_4$ aq., flow rate: 0.6 mL/min, oven temperature: 50° C.). Based on the analysis, the amount of erythritol in the liquid phase was calculated.

Figure 1:
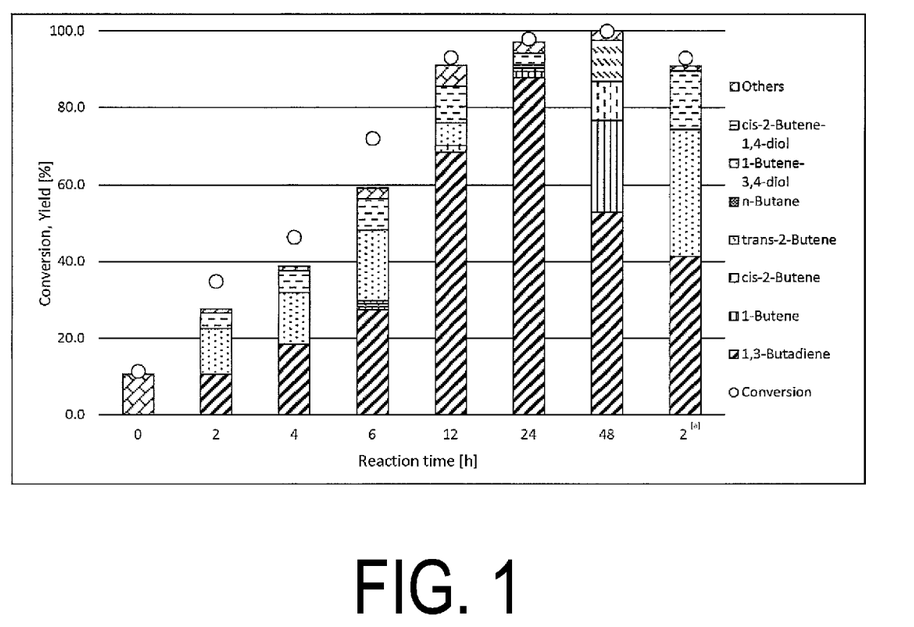
FIG. 1 is a graph illustrating the conversion in a reduction reaction of erythritol of Example 1 as well as the yield and selectivity of products.
Figure 2:
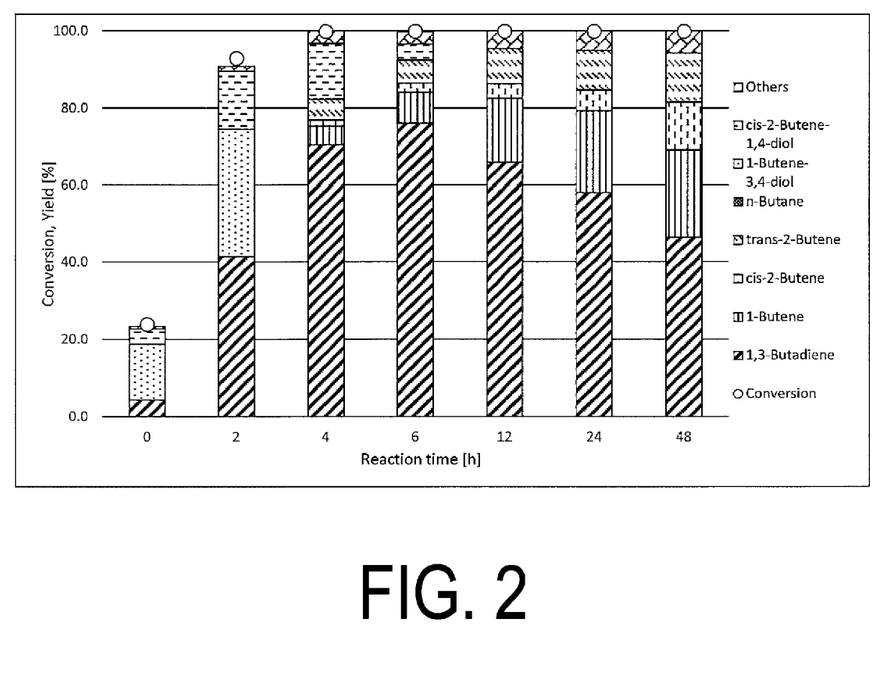
FIG. 2 is a graph illustrating the conversion in a reduction reaction of erythritol of Comparative Example 1 as well as the yield and selectivity of products.

Based on the amounts of erythritol and products contained in the gas phase and the liquid phase as analyzed by the gas phase analysis and the liquid phase analysis, the conversion of erythritol as well as the yield and selectivity of each of the products were calculated. The results of Example 1 are indicated in Table 1 and FIG. 1, and the results of Comparative Example 1 are indicated in Table 2 and FIG. 2, respectively. Note that "2[a]" in FIG. 1 indicates, as a comparison, the result of Reaction time=2 h in Comparative Example 1. The results of Example 2 (Entries 1 and 2) and Comparative Example 2 (Entry 3) are indicated in Table 3, Entry 4 in Table 3 indicates, as a comparison, the result of Reaction time=24 h in Example 1.

TABLE 1

| Entry | Reaction time [h] | Conversion [%] | 1,3-Butadiene Yield [%] | 1,3-Butadiene Sel. [%] | 1-Butene Yield [%] | 1-Butene Sel. [%] | cis-2-Butene Yield [%] | cis-2-Butene Sel. [%] | trans-2-Butene Yield [%] | trans-2-Butene Sel. [%] | n-Butane Yield [%] | n-Butane Sel. [%] | 1-Butene-3,4-diol Yield [%] | 1-Butene-3,4-diol Sel. [%] | cis-2-Butene-1,4-diol Yield [%] | cis-2-Butene-1,4-diol Sel. [%] | Others Yield [%] | Others Sel. [%] |
|---|---|---|---|---|---|---|---|---|---|---|---|---|---|---|---|---|---|---|
| 1 | 0 | 11.4 | 0.0 | 0.0 | 0.0 | 0.0 | 0.0 | 0.0 | 0.0 | 0.0 | 0.0 | 0.0 | 0.0 | 0.0 | 0.0 | 0.0 | 10.7 | 100.0 |
| 2 | 2 | 34.8 | 10.6 | 38.3 | 0.0 | 0.0 | 0.0 | 0.0 | 0.0 | 0.0 | 0.0 | 0.0 | 11.9 | 43.1 | 4.1 | 14.8 | 1.1 | 3.8 |
| 3 | 4 | 46.4 | 18.4 | 47.5 | 0.0 | 0.0 | 0.0 | 0.0 | 0.0 | 0.0 | 0.0 | 0.0 | 13.5 | 34.9 | 5.8 | 14.9 | 1.0 | 2.6 |
| 4 | 6 | 72.1 | 27.5 | 46.5 | 0.7 | 1.2 | 0.8 | 1.3 | 0.8 | 1.4 | 0.0 | 0.0 | 18.5 | 31.2 | 8.1 | 13.6 | 2.8 | 4.8 |
| 5 | 12 | 93.1 | 68.4 | 75.2 | 0.0 | 0.0 | 1.9 | 2.1 | 0.0 | 0.0 | 0.0 | 0.0 | 5.8 | 6.4 | 9.5 | 10.5 | 5.4 | 5.9 |
| 6 | 24 | 98.0 | 87.8 | 90.3 | 1.6 | 1.6 | 1.0 | 1.1 | 0.8 | 0.8 | 0.0 | 0.0 | 0.0 | 0.0 | 3.0 | 3.0 | 3.0 | 3.1 |
| 7 | 48 | 100.0 | 52.9 | 52.9 | 23.9 | 23.9 | 10.1 | 10.1 | 10.7 | 10.7 | 0.0 | 0.0 | 0.0 | 0.0 | 0.0 | 0.0 | 2.5 | 2.5 |

TABLE 2

| Entry | Reaction time [h] | Conversion [%] | 1,3-Butadiene Yield [%] | 1,3-Butadiene Sel. [%] | 1-Butene Yield [%] | 1-Butene Sel. [%] | cis-2-Butene Yield [%] | cis-2-Butene Sel. [%] | trans-2-Butene Yield [%] | trans-2-Butene Sel. [%] | n-Butane Yield [%] | n-Butane Sel. [%] | 1-Butene-3,4-diol Yield [%] | 1-Butene-3,4-diol Sel. [%] | cis-2-Butene-1,4-diol Yield [%] | cis-2-Butene-1,4-diol Sel. [%] | Others Yield [%] | Others Sel. [%] |
|---|---|---|---|---|---|---|---|---|---|---|---|---|---|---|---|---|---|---|
| 1 | 0 | 23.9 | 4.3 | 18.6 | 0.0 | 0.0 | 0.0 | 0.0 | 0.0 | 0.0 | 0.0 | 0.0 | 14.5 | 62.1 | 4.0 | 17.0 | 0.5 | 2.3 |
| 2 | 2 | 93.0 | 41.4 | 45.6 | 0.0 | 0.0 | 0.0 | 0.0 | 0.0 | 0.0 | 0.0 | 0.0 | 33.1 | 36.4 | 15.2 | 16.7 | 1.2 | 1.3 |
| 3 | 3 | 99.9 | 70.5 | 70.6 | 4.8 | 4.8 | 1.7 | 1.7 | 5.4 | 5.4 | 0.0 | 0.0 | 0.0 | 0.0 | 14.4 | 14.4 | 3.1 | 3.1 |
| 4 | 4 | 100.0 | 76.1 | 76.1 | 8.1 | 8.1 | 2.4 | 2.4 | 6.0 | 6.0 | 0.0 | 0.0 | 0.0 | 0.0 | 4.1 | 4.1 | 3.1 | 3.1 |
| 5 | 6 | 100.0 | 65.9 | 65.9 | 16.7 | 16.7 | 3.8 | 3.8 | 9.1 | 9.1 | 0.0 | 0.0 | 0.0 | 0.0 | 0.0 | 0.0 | 4.5 | 4.5 |
| 6 | 12 | 100.0 | 57.9 | 57.9 | 21.4 | 21.4 | 5.5 | 5.5 | 10.2 | 10.2 | 0.0 | 0.0 | 0.0 | 0.0 | 0.0 | 0.0 | 5.1 | 5.1 |
| 7 | 24 | 100.0 | 46.4 | 46.4 | 22.7 | 22.7 | 12.5 | 12.5 | 12.7 | 12.7 | 0.0 | 0.0 | 0.0 | 0.0 | 0.0 | 0.0 | 5.7 | 5.7 |

TABLE 3

| Entry | Solvent | Reaction time [h] | Conversion [%] | Selectivity/% | | | | | | |
|---|---|---|---|---|---|---|---|---|---|---|
| | | | | 1,3-Butadiene | 1-Butene | cis-2-Butene | trans-2-Butene | 1-Butene-3,4-diol | 2-Butene-1,4-diol | Others |
| 1 | None | 48 | 98 | 95.8 | 0.0 | 0.0 | 0.0 | 0.0 | 0.0 | 4.2 |
| 2 | None | 72 | 100 | 79.5 | 5.4 | 6.1 | 5.0 | 0.0 | 0.0 | 4.0 |
| 3 | 1,4-Dioxane | 24 | 99 | 66.3 | 0.0 | 0.0 | 0.0 | 20.6 | 12.3 | 0.8 |
| 4 | None | 24 | 98 | 90.3 | 1.6 | 1.1 | 0.8 | 0.0 | 3.0 | 3.1 |

In the examples and comparative examples described above, the conversion was calculated by Formula (1) below, the yield was calculated by Formula (2) below, and the selectivity was calculated by Formula (3) below, on the assumption that a carbon balance (C.B.) was 100%. The actual C.B. was from 93 to 97%.

Conversion (%)={amount (mol) of substrate charged−amount (mol) of remaining substrate}/amount (mol) of substrate charged×100     (1)

Yield (%) of substance $A$=amount (mol) of substance $A$ produced/{total amount (mol) of products+amount (mol) of remaining substrate}×100     (2)

Selectivity (%) of substance $A$=amount (mol) of substance $A$ produced/total amount (mol) of products×100     (3)

The above configurations of the present disclosure and variations thereof are summarized as Appendices listed below.

[Appendix 1] A method for producing an olefin, the method including reacting a compound including two adjacent carbon atoms each containing a hydroxy group with hydrogen and forming an olefin, in which the reaction of the compound including two adjacent carbon atoms each containing a hydroxy group with the hydrogen in the olefinating step proceeds in the presence of a catalyst under a condition substantially free of a solvent, the catalyst including a carrier, at least one oxide supported on the carrier and selected from the group consisting of oxides of group-6 elements and oxides of group-7 elements, and at least one metal supported on the carrier and selected from the group consisting of silver, iridium, and gold.

[Appendix 2] The method for producing an olefin according to Appendix 1, in which the compound including two adjacent carbon atoms each containing a hydroxy group is a liquid under the condition of the reaction, and the olefin is a gas under the condition of the reaction.

[Appendix 3] The method for producing an olefin according to Appendix 1, in which the compound including two adjacent carbon atoms each containing a hydroxy group includes a compound having two or more pairs of structures, each structure having two adjacent carbon atoms each containing a hydroxy group, and the olefin to be produced includes an olefin containing each of all the two or more pairs of the two adjacent carbon atoms forming a carbon-carbon double bond.

[Appendix 4] The method for producing an olefin according to Appendix 1, in which the compound including two adjacent carbon atoms each containing a hydroxy group includes a compound having two pairs of structures, each structure having two adjacent carbon atoms each containing a hydroxy group, and the olefin to be produced includes a diene.

[Appendix 5] The method for producing an olefin according to Appendix 1, in which the compound including two adjacent carbon atoms each containing a hydroxy group includes a compound having two pairs of structures adjacent to each other, each structure having two adjacent carbon atoms each containing a hydroxy group, and the olefin tip be produced includes a diene.

[Appendix 6] The method for producing an olefin according to Appendix 1, in which the compound including two adjacent carbon atoms each containing a hydroxy group includes erythritol, and the olefin to be produced includes 1,3-butadiene.

[Appendix 7] The method for producing an olefin according to any one of Appendices 1 to 6, in which the olefin is produced with a selectivity of 70% or greater (preferably 80% or greater) in the olefinating step.

[Appendix 8] The method for producing an olefin according to any one of Appendices 1 to 7, in which the at least one oxide selected from the group consisting of oxides of group-6 elements and oxides of group-7 elements includes rhenium oxide.

[Appendix 9] The method for producing an olefin according to any one of Appendices 1 to 8, in with the carrier includes at least one inorganic oxide (preferably cerium oxide) selected from the group consisting of cerium oxide, silica, magnesia, zinc oxide, alumina, zirconia, and titanic.

[Appendix 10] The method for producing an olefin according to any one of Appendices 1 to 9, in which the catalyst includes the carrier, a film of at least one oxide supported on the carrier and selected from the group consisting of oxides of group-6 elements and oxides of group-7 elements, and a film of at least one metal supported on the carrier and selected from the group consisting of silver, iridium, and gold.

[Appendix 11] The method for producing an olefin according to Appendix 10, in which the catalyst includes the film of the metal and the film of the oxide in this order on the carrier.

[Appendix 12] The method for producing an olefin according to any one of Appendices 1 to 11, in which a reaction time in the olefinating step is from 10 to 60 hours.

[Appendix 13] The method for producing an olefin according to any one of Appendices 1 to 12, in which a reaction temperature in the olefinating step is from 50 to 250° C.

[Appendix 14] The method for producing an olefin according to any one of Appendices 1 to 13, in which a content ratio of a solvent in a raw material mixture in the olefinating step is 0.1 parts by mass or less (preferably 0.05 parts by mass or less, and more preferably 0.01 parts by mass or less) based on a total amount (100 parts by mass) of the compound including two adjacent carbon atoms each containing a hydroxy group.

[Appendix 15] The method for producing an olefin according to any one of Appendices 1 to 14, in which the reaction in the olefinating step proceeds under conditions substantially free of water and an organic solvent (e.g., alcohols, sulfoxides, amides, ethers, esters, ketones, aliphatic hydrocarbons, alicyclic hydrocarbons, aromatic, hydrocarbons, and halogenated hydrocarbons).

[Appendix 16] A catalyst for an olefination reaction, the catalyst, to be used in a reaction of a compound including two adjacent carbon atoms each containing a hydroxy group with hydrogen forming an olefin, including a carrier, a film of at least one oxide supported on the carrier and selected from the group consisting of oxides of group-6 elements and oxides of group-7 elements, and a film of at least one metal supported on the carrier and selected from the group consisting of silver, iridium, and gold.

[Appendix 17] The catalyst for an olefination reaction according to Appendix 16, including the film of the metal and the film of the oxide in this order on the carder.

[Appendix 18] The catalyst for an olefination reaction according to any one of Appendices 16 or 17, in which the at least one oxide supported on the carrier and selected from the group consisting of oxides of group-6 elements and oxides of group-7 elements includes rhenium oxide.

[Appendix 19] The catalyst for an olefination reaction according to any one of Appendices 16 to 18, in which the carrier includes at least one inorganic oxide (preferably cerium oxide) selected from the group consisting of cerium oxide, silica, magnesia, zinc oxide, alumina, zirconia, and titania.

INDUSTRIAL APPLICABILITY

The method for producing an olefin and the catalyst in the present disclosure can be used in the production of an olefin using a vicinal diol as a raw material.

The invention claimed is:

1. A method for producing butadiene, the method comprising an olefinating step of reacting erythritol with hydrogen and forming the butadiene, wherein in the olefinating step, a reaction of the erythritol with the hydrogen proceeds in the presence of a catalyst under a condition substantially free of a solvent, wherein the catalyst is $ReO_X$—Au/CeO$_2$ or $ReO_X$—Ag/CeO$_2$.

2. The method for producing butadiene according to claim 1, wherein the erythritol is a liquid under the condition of the reaction, and the butadiene is a gas under the condition of the reaction.

3. The method for producing butadiene according to claim 1, wherein the erythritol includes two or more pairs of structures, each structure having two adjacent carbon atoms each containing a hydroxy group, and the butadiene to be produced contains two or more pairs of carbon-carbon double bonds.

4. The method for producing butadiene according to claim 1, wherein the erythritol includes two or more pairs of structures, each structure having two adjacent carbon atoms each containing a hydroxy group.

5. The method for producing butadiene according to claim 1, wherein the butadiene to be produced includes 1,3-butadiene.

6. The method for producing butadiene according to claim 1, wherein in the olefinating step, the butadiene is produced with a selectivity of 70% or greater.

7. The method for producing butadiene according to claim 1, wherein a reaction time in the olefinating step is from 10 to 60 hours.

8. The method for producing butadiene according to claim 1, wherein a reaction temperature in the olefinating step is from 50 to 250° C.

9. A catalyst for an olefination reaction, the catalyst, to be used in a reaction of erythritol with hydrogen forming butadiene, comprising a carrier, a film of at least one oxide supported on the carrier and selected from the group consisting of oxides of group-6 elements and oxides of group-7 elements, and a film of at least one metal supported on the carrier and selected from the group consisting of silver and gold,
wherein the at least one oxide supported on the carrier and selected from the group consisting of oxides of group-6 elements and oxides of group-7 elements includes rhenium oxide, and
wherein the carrier includes cerium oxide.

10. The method for producing butadiene according to claim 1, in which the erythritol includes two pairs of structures, each structure having two adjacent carbon atoms each containing a hydroxy group.

11. The method for producing butadiene according to claim 1, in which the catalyst includes a film of silver or gold and a film of cerium oxide in this order on a rhenium oxide carrier.

12. The method for producing butadiene according to claim 1, in which a content ratio of a solvent in a raw material mixture in the olefinating step is 0.1 parts by mass or less based on a total amount (100 parts by mass) of the erythritol.

13. The method for producing butadiene according to claim 1, in which a content ratio of a solvent in a raw material mixture in the olefinating step is 0.05 parts by mass or less, based on a total amount (100 parts by mass) of the erythritol.

14. The method for producing butadiene according to claim 1, in which the reaction in the olefinating step proceeds under conditions substantially free of water and an organic solvent.

15. The catalyst for an olefination reaction according to claim 9, including the film of the metal and the film of the oxide in this order on the carrier.

* * * * *